US006979451B1

(12) United States Patent
de la Fuente et al.

(10) Patent No.: US 6,979,451 B1
(45) Date of Patent: Dec. 27, 2005

(54) RECOMBINANT ANTIGEN MSP1A FROM ANAPLASMA MARGINALE TO REDUCE INFECTIONS IN TICKS, VACCINE COMPOSITIONS AND METHODS OF USE

(75) Inventors: Jose de Jesus de la Fuente, Stillwater, OK (US); Katherine M. Kocan, Perkins, OK (US); Jose Carlos Garcia-Garcia, Stillwater, OK (US); Edmour F. Blouin, Perkins, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 63 days.

(21) Appl. No.: 10/285,319

(22) Filed: Oct. 31, 2002

Related U.S. Application Data (63) Continuation-in-part of application No. 10/002,636, filed on Oct. 26, 2001.
(60) Provisional application No. 60/244,333, filed on Oct. 30, 2000.

(51) Int. Cl.[7] .................. A61K 39/00; A61K 39/002; A61K 39/38; A01N 63/00; A01N 65/00

(52) U.S. Cl. .................. 424/265.1; 424/266.1; 424/184.1; 424/191.1; 424/93.1

(58) Field of Search .................. 424/184.1, 265.1, 424/191.1, 266.1, 93.1, 235.1

(56) References Cited

U.S. PATENT DOCUMENTS

| 3,674,860 A | * | 7/1972 | Welter et al. |
| 4,956,278 A | | 9/1990 | Hart et al. ..................... 435/30 |
| 5,549,898 A | | 8/1996 | McGuire et al. ......... 424/269.1 |
| 5,798,219 A | | 8/1998 | Knowles et al. ........... 435/7.93 |
| 5,869,335 A | | 2/1999 | Munderloh et al. ......... 435/348 |
| 6,025,338 A | | 2/2000 | Barbet et al. ................. 514/44 |
| 6,242,571 B1 | * | 6/2001 | Knowles et al. |
| 2002/0127242 A1 | * | 9/2002 | de la Fuente et al. |

FOREIGN PATENT DOCUMENTS

| EP | 196290 | * | 10/1986 | |
| EP | 0196290 A2 | | 10/1986 | ........... C12P/21/00 |
| WO | WO97/08296 | * | 3/1997 | |
| WO | WO 97/08296 | | 3/1997 | ............ C12N/5/06 |

OTHER PUBLICATIONS de la Fuente et al, Expert Rev. Vaccines, 2003, 2/4:583–593.*
Almazan et al, Vaccine, 2003, 21:1492–1501.*
de la Fuente et al, Vet. Microbiology, 2002, 89:239–251.*
Camacho–Nuez et al Infection and Immunity 68/4:1946–1952, Apr. 2000.*
Brown et al, Infection and Immunity 66/11:5414–5422, Nov. 1998.*
Palmer et al Infection and Immunity 50/3:881–886, Dec. 1985.*
Arulkanthan et al, Infection and Immunity 67/7:3481–3487, Jul. 1999.*
McGuire et al, Vaccine, 12/5:465–471, 1994.
Bowie et al, Gene, 282:95–102, 2002.
Brown et al, Infection and Immunity 69/11:6853–6862, Nov. 2001.
de la Fuente et al, International J Parasitology 31:1705–1714, 2001.
Palmer et al, Parasitology Today 15/7:281–286, 1999.*
Vidotto et al, Infection and Immunity, 62/7:2940–2946, Ju. 1994.*
de la Fuente, J., J.C. Garcia–Garcia, E.F. Blouin, S.D. Rodriguez, M.A. Garcia, and K.M. Kocan. 2001. Evolution and function of tandem repeats in the major surface protein 1a of the ehrlichial pathogen *Anaplasma marginale*. *Animal Health Research Reviews*. 2:2:163–173.
de la Fuente, J., J.C. Garcia–Garcia, E.F. Blouin, B.R. McEwen, D. Clawson, and K.M. Kocan. 2001. Major surface protein 1a effects tick infection and transmission of the ehrlichial pathogen *Anaplasma marginale*. *International Journal for Parasitology*. 31:1705–1714.
de la Fuente, J., J.C. Garcia–Garcia, E.F. Blouin, and K.M. Kocan. 2003, Characterization of the functional domain of major surface protein 1a involved in adhesion of the rickettsia *Anaplasma marginate* to host cells. *Veterinary Microbiology*. 91:265–283.
de la Fuente, J., K.M. Kocan, J.C. Garcia–Garcia, E.F. Blouin, P.L. Claypool, and J.T. Saliki. 2002. Vaccination of cattle with *Anaplasma marginale* derived from tick cell culture and bovine erythrocytes followed by challenge–exposure by infected ticks. *Veterinary Microbiology*, 89:239–251.

(Continued)

*Primary Examiner*—N. M. Minnifield
(74) *Attorney, Agent, or Firm*—Fellers, Snider, Blankenship, Bailey & Tippens, P.C.

(57) ABSTRACT

Vaccines and methods for inducing an immune response in a ruminant. The vaccine composition including pathogen and tick-derived antigens and a carrier or diluent. The method for inducing an immune response in a ruminate to provide immune protection which reduces the infection of ticks by *A. marginale* and/or prevents the transmission of the pathogen includes the steps of administering to the ruminant an effective amount of the vaccine composition having at least one antigen member of the group comprising at least one antigen member of the group comprising (i) recombinant MSP1a surface protein antigen of *A. marginale*, (ii) a subunit of recombinant MSP1a surface protein antigen of *A. marginale* and (iii) recombinant MSP1a surface protein antigen or subunits thereof in combination with antigen preparation derived from *A. marginale* infected cultured tick IDE8 cells and/or other pathogen and tick-derived antigens, and a carrier or diluent.

7 Claims, 1 Drawing Sheet

OTHER PUBLICATIONS

Eid, G., D.M. French, A.M. Lundgren, A.F. Barbet, T.F. McElwain, and G.H. Palmer. 1996. Expression of Major Surface Protein 2 Antigenic Variants during Acute *Anaplasma marginale* Rickettsemia. *Infection and Immunity.* 64:3:836–841.

Kocan, K.M. 1986. Development of *Anaplasma marginale* Theiler in ixodid ticks: Coordinated development of rickettsial organisms and its tick host. In: Sauer Jr, Hair JA, editors. *Morphology, Physiology and Behavioral Ecology of Ticks.* Chichester: Horwood, pp. 472–505.

Kocan, K.M., E.F. Blouin, G.H. Palmer, I.S. Eriks, W.L. Edwards, and P.L. Claypool. 1996. Preliminary studies on the effect of *Anaplasma marginale* antibodies ingested by *Dermacentor andersoni* ticks (Acari:Ixodidae) with their blood meal on infections in salivary glands. *Experimental & Applied Acarology.* 20:297–311.

Arulkanthan, A., W.C. Brown, T.C. McGuire, and D.P. Knowles. 1999. Biased Immunoglobulin G1 Isotype Responses Induced in Cattle with DNA Expressing *msp*1a of *Anaplasma marginale*. *Infection and Immunity.* 67:7:3481–3487.

Barbet, A.F., R. Blentlinger, J. Yi, A.M. Lundgren, E.F. Blouin, and K.M. Kocan. 1999. Comparison of surface proteins of *Anaplasma marginale* grown in tick cell culture, tick salivary glands, and cattle. *Infection and Immunity.* 67:1:102–107.

Blouin, E.F., J.T. Saliki, J. de la Fuente, J.C. Garcia–Garcia, K.M. Kocan. 2002b. Antibodies to *Anaplasma marginale* major surface protein 1a and 1b inhibit infectivity for cultured tick cells. *Veterinary Parasitology.* 111:247–260.

Bowie, M.V., J. de la Fuente, K.M. Kocan, E.F. Bouin, and A.F. Barbet. 2002. Conservation of major surface protein 1 genes of *Anaplasma marginale* during cyclic transmission between ticks and cattle. *Gene* 282:95–102.

Brown, W.C., D. Zhu, V. Shkap, T.C. McGuire, E.F. Blouin, K.M. Kocan, and G.H. Palmer. 1998. The Repertoire of *Anaplasma marginale* Antigens Recognized by $CD4^+$ T–Lymphocyte Clones from Protectively Immunized Cattle Is Diverse and Includes Major Surface Protein 2 (MSP–2) and MSP–3. *Infection and Immunity*, 66:11:5414–5422.

Brown, W.C., G.H. Palmer, H.A. Lewin, and T.C. McGuire. 2001. $CD4^+T$ Lymphocytes from Calves Immunized with *Anaplasma marginale* Major Surface Protein 1 (MSP1), a Heteromeric Complex of MSP1a and MSP1b, Preferentially Recognize the MSP1a Carboxyl Terminus That Is Conserved among Strains. *Infection and Immunity.* 69:11:6853–6862.

Camacho–Nuez, M., M. de L. Muñoz, C.E. Suarez, T.C. McGuire, W.C. Brown, and G.H. Palmer. 2000. Expression of Polymorfic *msp1*β Genes during Acute *Anaplasma marginale* Rickettsemia. *Infection and Immunity*, 68:4:1946–1952.

Kocan, K.M., T. Halbur, E.F. Blouin, V. Onet, J. de la Fuente, J.C. Garcia–Garcia, and J.T. Saliki. 2001. Immunization of cattle with *Anaplasma marginale* derived from tick cell culture. *Veterinary Parasitology.* 102:151–161.

McGuire, T.C., E.B. Stephens, G.H. Palmer, T.F. McElwain, C.A. Lichtensteiger, S.R. Leib, and A.F. Barbet. 1994. Recombinant vaccinia virus expression of *Anaplasma marginale* surface protein MSP–1a: effect of promoters, leader sequences and GPI anchor sequence on antibody response. *Vaccine.* 12:5:465–471.

Montenegro–James, S., M.A. James, M. Toro Benitez, E. Leon, B.K. Baek, and A.T. Guillen. 1991. Efficacy of purified *Anaplasma marginale* initial bodies as a vaccine against anaplasmosis. *Parasitology Research.* 77:93–101.

Palmer, G.H., K.M. Kocan, S.J. Barron, J.A. Hair, A.F. Barbet, W.C. Davis, and T.C. McGuire. 1985. Presence of Common Antigens, Including Major Surface Protein Epitopes, between the Cattle (Intraerythrocytic) and Tick Stages and *Anaplasma marginale*. *Infection and Immunity.* 50:3:881–886.

Palmer, G.H., F.R. Rurangirwa, K.M. Kocan, and W.C. Brown. 1999. Molecular Basis for Vaccine Development against the Ehrlichial Pathogen *Anaplasma marginale*. *Parasitology Today.* 15:7:281–286.

Palmer, G.H., F.R. Rurangirwa, and T.F. McElwain. 2001. Strain Composition of the Ehrlichia *Anaplasma marginale* within Persistently Infected Cattle, a Mammalian Reservoir for Tick Transmission. *Journal of Clinical Microbiology.* 39:2:631–635.

Vidotto, M.C., T.C. McGuire, T.F. McElwain, G.H. Palmer, and D.P. Kowles, Jr. 1994. Intermolecular Relationships of Major Surface Proteins of *Anaplasma marginale*. *Infection and Immunity.* 62:7:2940–2946.

Allred DR, McGuire TC, Palmer GH, Leib SR, Harkins TM, McElwain TF, Barbet AF. Molecular basis for surface antigen size polymorphisms and conservation of a neutralization–sensitive epitope in *Anaplasma marginale*. Proc Natl Acad Sci USA 1990; 87: 3220–3224.

Barbet AF, Blentlinger R, Jooyoung Y, Lundgren AM, Blouin EF, Kocan KM. Comparison of surface proteins of *Anaplasma marginale* grown in tick cell culture, tick salivary glands, and cattle. Infect Immun 1999; 67:102–107.

Barbet AF, Palmer GH, Myler PJ, McGuire TC. Characterization of an immunoprotective protein complex of *Anaplasma marginale* by cloning and expression of the gene coding for polypeptide AM 105L. Infect Immun 1987;55:2428–2435.

Blouin EF, Barbet AF, Jooyoung Y, Kocan KM, Saliki JT. Establishment and characterization of an Oklahoma isolate of *Anaplasma marginale* in cultured *Ixodes scapularis* cells. Vet Parasitol 1999; 87:301–313.

Blouin EF, Kocan KM. Morphology and development of *Anaplasma marginale* (Rickettsiales: Analplasmataceae) in cultured *Ixodes scapularis* (Acari:Ixodidae) cells. J Med Entomol 1998; 35:788–797.

De la Fuente J, Garcia–Garcia JC, Blouin EF, Kocan KM. Differential adhesion of major surface proteins 1a and 1b of the ehrlichial cattle pathogen *Anaplasma marginale* to bovine erythrocytes and tick cells. Int. J. Parasitol. 2001;31: 145–153.

De la Fuente J, Van Den Bussche RA, Kocan KM. Molecular phylogeny and biogeography of North American isolates of *Anaplasma marginale* (Rickettsiaceae: Ehrlichieae). Vet Parasitol 2001; 97:65–76.

Kocan KM, Blouin EF, Barbet AF. Anaplasmosis control: past, present and future. Ann NY Acad Sci, 2000; 916:501–509.

McGarey DJ, Allred Dr. Characterization of hemagglutinating components on the *Anaplasma marginale* initial body surface and identification of possible adhesins. Infect Immum 1994; 62:4587–4593.

McGarey DJ, Barbet AF, Palmer GH, McGuire TC, Allred DR. Putative adhesins of *Anaplasma marginale*: major surface polypeptides 1a and 1b. Infect Immun 1994; 62:4594–4601.

Munderloh UG, Blouin EF, Kocan KM, Ge NL. Establishment of the tick (Acari: Ixodidae)–borne cattle pathogen *Anaplasma marginale* (Rickettsiales: Anaplasmataceae) in tick cell culture. J Med Ent 1996; 33: 656–664.

Oberle SM, Palmer GH, Barbet AF, McGuire TC. Molecular size variations in an immunoprotective protein complex among isolates of *Anaplasma marginale*. Infect Immun 1988; 56:1567–1573.

Palmer GH, Barbet AF, Cantor GH, McGuire TC. Immunization of cattle with the MSP–1 surface protein complex induces protection against a structurally variant *Anaplasma marginale* isolate. Infect Immun 1989; 57:3666–3669.

Palmer GH, McElwain TF. "Molecular basis for vaccine development against anaplasmosis and babesiosis." Vet Parasitol: 1995;57:233–253.

Palmer GH, Waghela SD, Barbet AF, Davis WC, McGuire TC. Characterization of a neutralization–sensitive epitope on the AM 105 surface protein of *Anaplasma marginale* . J Parasitol 1987; 17:1279–1285.

Viseshakul N, Kamper S, Bowie MV, Barbet AF. Sequence and expression analysis of a surface antigen gene family of the rickettsia *Anaplasma marginale*. Gene 2000; 253:45–53.

* cited by examiner

RECOMBINANT ANTIGEN MSP1A FROM ANAPLASMA MARGINALE TO REDUCE INFECTIONS IN TICKS, VACCINE COMPOSITIONS AND METHODS OF USE

CROSS REFERENCE TO RELATED APPLICATION

This application is a continuation-in part of prior filed, copending U.S. patent application Ser. No. 10/002,636, filed Oct. 26, 2001 which claims the benefit of U.S. provisional patent application Ser. No. 60/244,333, filed Oct. 30, 2000, both of which are hereby incorporated by reference.

BACKGROUND OF THE INVENTION

1. Technical Field

The present invention relates to recombinant *Anaplasma marginale* major surface protein (MSP)1a, related vaccines and methods useful to reduce infections in ticks and affect the biological transmission of the pathogen of the species *A. marginale*.

2. Background

Anaplasmosis is a tick-borne disease of cattle caused by *Anaplasma marginale* (Rickettsiales: Anaplasmataceae). The only known site of development of *A. marginale* in cattle is within erythrocytes [1]. The number of infected erythrocytes increases logarithmically during infection and removal of infected erythrocytes by phagocytic cells of the reticuloendothelial system often results in development of anemia and icterus without hemoglobinemia and hemoglobinuria [2]. While mechanical transmission of *A. marginale* occurs when infected blood is transferred from infected to susceptible animals by biting flies or blood-contaminated fomites, biological transmission is effected by feeding ticks. Approximately 20 species of ticks have been incriminated as vectors worldwide [3, 4]. Cattle that recover from acute infection remain persistently infected and develop life-long immunity against clinical disease, but they serve as reservoirs of infection for mechanical and/or biological transmission by ticks.

The development of *A. marginale* in ticks is complex and coordinated with the tick feeding cycle [5, 6, 8]. In the cycle of *A. marginale* that was described in male ticks transferred from infected to susceptible hosts, the first site of infection occurs in tick gut cells. After the ticks feed a second time, many other tick tissues become infected, including the salivary glands from where the rickettsiae are transmitted to cattle during feeding. Male ticks become persistently infected with *A. marginale* and are able to transmit *A. marginale* to multiple hosts [6, 7, 8].

Major surface protein (MSP)1a is one of six MSPs that have been described on *A. marginale* derived from bovine erythrocytes [9]. MSP1a forms the MSP1 complex with MSP1b [10, 11]. MSP1a is encoded by a single gene, msp1α, which is conserved during the multiplication of the bacterium in cattle and ticks [12, 13]. This protein is variable in molecular weight among geographic isolates because of varying numbers of tandem 28 or 29 amino acid repeats located in the amino terminal portion of the protein [11, 14, 15]. MSP1a was shown to be an adhesin for bovine erythrocytes and for both native and cultured tick cells using recombinant *E. coli* expressing MSP1a in microtiter hemagglutination and adhesion recovery assays and by microscopy [16, 17, 18]. Furthermore, MSP1a was shown to effect infection and transmission of *A. marginale* by *Dermacentor* spp. ticks [19] and was also shown to be involved in bovine immunity to *A. marginale* infection [20, 21, 22, 26]. See also U.S. Pat. No. 10/002,636, incorporated herein by reference.

Recently, we demonstrated that infection of *A. marginale* for cultured tick cells was inhibited by antibodies against recombinant MSP1a [23, 24]. While antisera from cattle naturally infected with *A. marginale* did not inhibit *A. marginale* infection, antibodies produced in rabbits and cattle immunized with the recombinant MSP1a effected inhibition of *A. marginale* infection for the cultured tick cells [24]. This inhibitory effect has also been demonstrated using antibodies against a synthetic MSP1a repeated peptide, and this data provided additional evidence that MSP1a plays a role in adhesion of *A. marginale* to tick cells [15].

Vaccination is the most efficient and economical method for control of anaplasmosis, and development of effective vaccines has been a priority of the cattle industry worldwide [9]. Infected bovine erythrocytes have been the only source of vaccine antigen until recently when a tick cell culture system was developed for propagation of *A. marginale* and provides an alternative antigen source. The cell culture-derived *A. marginale* is currently being tested as antigen for use in vaccine development [20, 22]. See also U.S. Pat. No. 5,869,335, incorporated herein by reference.

Thus far, vaccines using erythrocyte or cell culture-derived antigens have effected reduction of clinical disease but have not prevented infection of cattle [9, 20, 22, 25, 27, 28, 37]. Also, antibodies in cattle immunized with erythrocyte-derived *A. marginale* have not caused reduction of *A. marginale* infections in ticks [7].

The desired result of a vaccine for the control of anaplasmosis is to have a protection effect on the multiplication of *A. marginale* in the bovine host and a blocking effect on the transmission of the pathogen by the tick vector. Existing vaccines and experimental vaccines, however, including formulations using the recombinant MSP1a, the MSP1 complex and partially purified parasites from infected erythrocytes and cultured tick cells (see U.S. Pat. Nos. 5,549,898; 5,869,335 and 10/002,636 incorporated herein by reference) have not demonstrated any effect on the infection of the tick vector by the pathogen. Therefore, it is desirable to develop vaccines against anaplasmosis with protection effect on the multiplication of *A. marginale* in the bovine host and an effect on the transmission of the pathogen by the tick vector.

A better understanding of the present invention, its several aspects, and its advantages will become apparent to those skilled in the art from the following detailed description, taken in conjunction with the attached figures, wherein there is described the preferred embodiment of the invention, simply by way of illustration of the best mode contemplated for carrying out the invention.

DETAILED DESCRIPTION OF THE INVENTION

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

In accordance with the present invention there is provided a new vaccine against the rickettsial cattle pathogen *A. marginale* through the use of discrete recombinant MSP1a and polypeptides derived from MSP1a containing the immunoprotective and functional regions that are expressed in *E.coli*. In one aspect, only recombinant MSP1a or immunoprotective and functional regions thereof are utilized as the antigenic component of the vaccine. In another aspect, recombinant MSP1a or subunits thereof are utilized in combination with other antigen preparations, particularly antigen preparations derived from *A. marginale*-infected cultured tick IDE8 cells. Another aspect of the present invention relates to recombinant *A. marginale* major surface protein (MSP)1a, related vaccines and methods useful to reduce infections in ticks and affect the biological transmission of the pathogen of the species *A. marginale*.

MSP1a and MSP1b are isolated from *A. marginale* initial bodies as a complex of two noncovalently linked, antigenically distinct polypeptides. It is possible that the association between MSP1a and MSP1b in the surface protein complex allows the parasite to more effectively bind to erythrocyte and/or tick cell components. MSP1a could be the essential subunit in the recognition of the tick cell receptor, while the binding to the erythrocyte receptor could be mediated primarily by MSP1b or by both protein subunits through the binding of distinct erythrocyte components. Additionally, the association between MSP1a and MSP1b could stabilize and/or properly conform the MSP1 complex [29].

MSP1a is encoded by a single monocystronic gene, msp1α, which is polymorphic among geographical isolates of *A. marginale* [30, 31, 32]. *A. marginale* isolates differ in the number of 28–29 amino acids tandem repeats within the MSP1a polypeptide [31, 32], which contain a neutralization-sensitive epitope [33, 31]. However, the sequence of msp1α does not change during the multiplication of the parasite in the bovine host and the tick vector. The second MSP1 subunit, MSP1b, is encoded by at least two monocystronic genes, msp1β1 and msp1β2 [34]. These loci are polymorphic between and within populations of *A. marginale* from different geographical regions and life cycle stages but conserve a high degree of similarity. Sequence diversity is mainly due to point mutations in variable regions, perhaps due to selective immune pressure. The genetic structure of msp1α together with the vital function of codified polypeptides permits the inclusion of recombinant MSP1a polypeptides, or its functional domains, in vaccine formulations against *A. marginale*.

The experiments described and examples provided hereinafter demonstrate that cattle immunized with recombinant MSP1a alone or in combination with tick cell culture derived *A. marginale* are unexpectedly better protected against *A. marginale* infection as demonstrated by a lower reduction in packed cell volume (PCV) and lower peak parasitemia (PPE) than cattle immunized with the MSP1 complex, a combination of uncomplexed MSP1a and MSP1b surface protein antigens, the MSP1b antigen alone, cell culture derived *A. marginale*, or cell culture derived *A. marginale* combined with MSP1b. Indeed, only erythrocyte-derived *A. marginale* appears to confer like protection.

EXAMPLE 1

Preparation of Recombinant *E. coli* Expressing MSP1a and Preparation of Antigen The msp1α gene was cloned by PCR from the Oklahoma isolate of *A. marginale* derived from infected erythrocytes. DNA was extracted from 1 ml stored blood samples containing infected bovine erythrocytes collected during high parasitemia employing 250 μL Tri Reagent (Sigma) and following manufacturer's recommendations. Extracted DNA was resuspended in 100 μL water. The msp1α gene was amplified from 1 μL DNA by PCR using 10 pmol of each primer MSP1aP: 5'GCATTACAACGCAACGCT-TGAG3' (SEQ. ID NO: 1) and MSP1a3: 5'GCTTTACGC-CGCCGCCTGCGCC3' (SEQ. ID NO: 2) in a 50-μL volume PCR employing the Access RT-PCR system (Promega). Reactions were performed in an automated DNA thermal cycler (Eppendorf) for 35 cycles. After an initial denaturation step of 30 sec at 94° C., each cycle consisted of a denaturing step of 30 sec at 94° C. and an annealing-extension step of 2.5 min at 68° C. The program ended by storing the reactions at 4° C. PCR products were electrophoresed on 1% agarose gels to check the size of amplified fragments. The amplified fragments were resin purified from PCR reactions (Wizard Promega) and cloned into pGEM-T vector (Promega) for sequencing both strands (Core Sequencing Facility, Department of Biochemistry and Molecular Biology, Noble Research Center, Oklahoma State University).

For high level expression of MSP1a, msp1α coding region was amplified from per1 (msp1α in pGEM-T vector) plasmid DNA by PCR using the primers 5'CCGCTC-GAGATGTTAGCGGAGTATGTGTCC3' (SEQ. ID NO: 3) and 5'GAAGATCTCGCCGCCGCCTGCGCC3' (SEQ. ID NO: 4). The msp1α amplification product was digested with XhoI and BglII and inserted into the cloning site of pFLAG-CTC expression vector (Sigma). Recombinant plasmid was named pFLC1a. In this construct, the inserted gene is under the control of the inducible tac promoter and yield full-length MSP1a polypeptide, with a C-terminal fusion of a FLAG marker octapeptide. The fidelity and orientation of the construct was verified by sequencing. For expression of MSP1a recombinant polypeptides, pFLC1a expression plasmid was transformed into *E. coli* K-12 (strain JM109). Transformed *E. coli* strains were inoculated in LB containing 50 μg/ml Ampicillin and 0.4% glucose. Cultures were grown at 37° C. to $OD_{600nm}$=0.4. IPTG was then added to 0.5 mM final concentration, and incubation continued during 4 h, for induction MSP1a expression. Cells were collected by centrifugation and membranes extracted after sonication and centrifugation. MSP1b was cloned, expressed and purified in a similar way. Doses of 5 ml containing 100 μg recombinant antigens were used for vaccination in subsequent studies.

EXAMPLE 2

Analysis of the Protective Capacity of Vaccine Preparations Containing Recombinant MSP1a 1. Propagation of *Anaplasma marginale* in tick cell culture and preparation of immunogen. The IDE8 (ATCC CRL 11973) tick cell line derived from embryos of *Ixodes scapularis* was maintained at 31° C. in L-15B medium, pH 7.2, supplemented with 5% heat inactivated fetal bovine serum (FBS; Sigma, USA), 10% tryptose phosphate broth (Difco, USA) and 0.1% bovine lipoprotein concentrate (ICN, USA). Cultures were grown in 25-cm² plastic flasks (Nunc, Rosekilde, Denmark) with 5 ml of medium, and the medium was replaced weekly. The cells were subcultured at 1:5 to 1:20, and the cells became tightly adherent to the culture substrate and multiplied with a population doubling time of 3 to 5 days to a density of about 5×10⁶ cells/ml. Nearly confluent monolayers from each passage were collected and stored in liquid nitrogen in medium with 10% DMSO.

Tick cell cultures infected with the Oklahoma isolate of *A. marginale* were propagated. Terminal cell cultures were harvested, the cells centrifuged, and the contents of each T25 flask was resuspended in 1 ml PBS and stored at −70° C. until used as antigen for immunogen doses. The antigen aliquots were thawed, pooled and a sample was taken and tested by indirect ELISA. The cell culture-derived antigen was inactivated with beta propiolactone (BPL) and the volume was adjusted to 5 ml so that each dose contained approximately $2\times10^{10}$ *A. marginale*.

2. Preparation of *A. marginale* antigen from bovine erythrocytes. Two susceptible, splenectomized calves (PA432 and PA433) were each inoculated with 2.5 ml blood stabilate (40% parasitemia) collected from a calf with the Virginia isolate of *A. marginale*. The calves were monitored for infection by examination of stained blood smears. Blood was collected from PA432 at parasitemias of 13.6% and 32.7% and from PA433 at parasitemias of 12.2% and 12.9%. After each collection, the erythrocytes were washed 3 times in PBS, each time removing the buffy coat. The erythrocytes were frozen at −70° C. 1:1 in RPMI 1640 cell culture medium until used as antigen for the immunization studies. The frozen erythrocyte antigen was thawed, washed in PBS, and centrifuged. The resulting pellet was washed to remove the hemoglobin, after which the antigen was pooled and inactivated with β-propiolactone (BPL). An aliquot was tested by ELISA as described previously for the erythrocyte antigen preparation using a known erythrocyte standard. Doses (5 ml) were prepared that contained approximately $2\times10^{10}$ *A. marginale*.

3. Experimental design. Fifty, 16-month month old Angus cattle were randomly assigned into ten groups of five cattle each that were immunized with various antigens as follows. (1) MSP1 complex, (2) MSP1a and MSP1b, (3) MSP1a, (4) MSP1b, (5) cell culture-derived *A. marginale*, (6) cell culture-derived *A. marginale* and MSP1a, (7) cell culture-derived *A. marginale* and MSP1b, (8) erythrocyte-derived *A. marginale*, (9) uninfected IDE8 tick cells and (10) adjuvant only.

4. Immunizations. All cattle were immunized 3 times by subcutaneous injection of the antigen at weeks 1, 4 and 6. Each antigen dose was 5 ml in volume and contained an antigen in the adjuvant, XTEND® III (Grand Laboratories, Larchwood, Iowa). All cattle were challenge-exposed 10 weeks after the last immunization with $1\times10^7$ *A. marginale* infected erythrocytes collected from a calf experimentally infected with the Oklahoma isolate of *A. marginale*. Blood of the immunized and control cattle was monitored for infection with *A. marginale* by microscopic examination of blood smears and hematology was done daily after the onset of infection. Parameters evaluated in cattle included determination of the peak percent infected erythrocytes (PPE), percent reduction in the packed cell volume (PCV), and the prepatent period (days) determined from the day of challenge-exposure to the onset of infection.

5. Collection of blood and serum samples. Whole blood was collected in vacutainer tubes containing EDTA and used for preparation of stained blood smears for light microscopy and for determination of the PCV. Serum samples were collected from each animal before immunization, weekly until the cattle were challenge-exposed and daily after cattle developed parasitemia as a result of challenge-exposure. Serum samples were stored at −70° C. until tested by competitive ELISA and Western blots.

6. Characterization of the immune response in vaccinated cattle by competitive ELISA and Western blots. Antibody responses of all immunized and control cattle at two weeks after the last immunization to MSP1a, MSP1b and MSP5 were determined using ELISAs specific for detection of antibodies to each of these MSPs. Antibody responses of all immunized and control cattle at two weeks after the last immunization to MSP1a and MSP1b were also analyzed by Western blot. One hundred micrograms of recombinant MSP1a or MSP1b were loaded in an 8% polyacrylamide gel. SDS-PAGE gels were transferred to a nitrocellulose membrane. The membrane was blocked with 5% skim milk for 1 hr at room temperature. Sera from immunized cattle was diluted 1:200 in TBS. Serum from an uninfected bovine was included as a negative control. All sera were incubated with the membrane for 1 hr at room temperature using a Mini-Protean II Multi-screen (BioRad, USA). The membrane was washed 3 times with TBST and incubated for 1 hr at room temperature with goat anti-rabbit IgG alkaline phosphatase conjugate (KPL, USA) diluted 1:10,000. The membrane was washed again and the color developed using Sigma Fast BCIP/NBT alkaline phosphatase substrate tablets. The membrane was then examined for recognition of the bands corresponding to MSP1a and MSP1b.

7. Statistical analysis. For the analysis of results from the immunization experiment, pairwise comparisons (Student's t test) were conducted to compare results between cattle immunized with antigen preparations and the controls. Parameters analyzed included the prepatent period (days), the peak percent parasitized erythrocytes (PPE) and the percent reduction in the packed cell volume (PCV). Mean antibody levels were compared using an ANOVA test.

Figure 1:
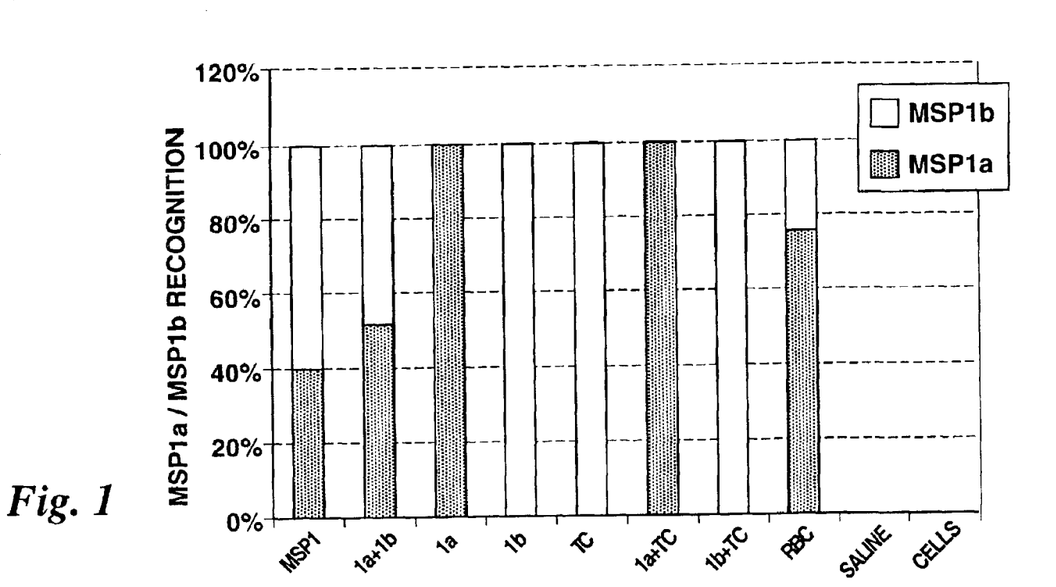
FIG. 1 is a graphical illustration of the immune response against MSP1a and MSP1b determined by Western blot analysis of sera derived from immunized cattle and controls generated in connection with the experimental results reported herein.

8. Results. Antibody titers against MSP1a, MSP1b and MSP5 in immunized cattle peaked two weeks after the last immunization. The immune response against MSP1a, MSP1b and MSP5 was analyzed by Western blot. Cattle immunized with recombinant antigen preparations responded to recombinant proteins included on each preparation (FIG. 1). Cattle immunized with tick cell derived *A. marginale* antigens and with infected erythrocytes-derived antigens recognized primarily MSP1b or MSP1a, respectively (FIG. 1).

Protection was evaluated using the reduction in PCV, the PPE and the prepatent period. No differences were observed in the prepatent period. The PPE was reduced in cattle immunized with MSP1a, MSP1b, the combination of recombinant antigens with infected tick cells-derived antigens and in animals immunized with infected erythrocytes-derived antigens as shown in Table 1.

TABLE 1

| Group | Peak Parasitemia (%) | | |
| --- | --- | --- | --- |
| | Ave | SD | P |
| MSP1 | 5.5 | 2.8 | 0.13 |
| 1a + 1b | 6.0 | 1.6 | 0.14 |
| 1a | 4.8 | 0.6 | 0.03 |
| 1b | 3.9 | 1.0 | 0.01 |
| TC | 4.1 | 2.3 | 0.03 |
| 1a + TC | 4.7 | 1.4 | 0.03 |
| 1b + TC | 3.9 | 0.8 | 0.01 |

TABLE 1-continued

| Group | Peak Parasitemia (%) | | |
| --- | --- | --- | --- |
| | Ave | SD | P |
| RBC | 2.7 | 1.1 | 0.004 |
| Saline | 5.5 | 1.4 | 0.08 |
| Cells | 7.4 | 2.3 | — |

Figure 2:
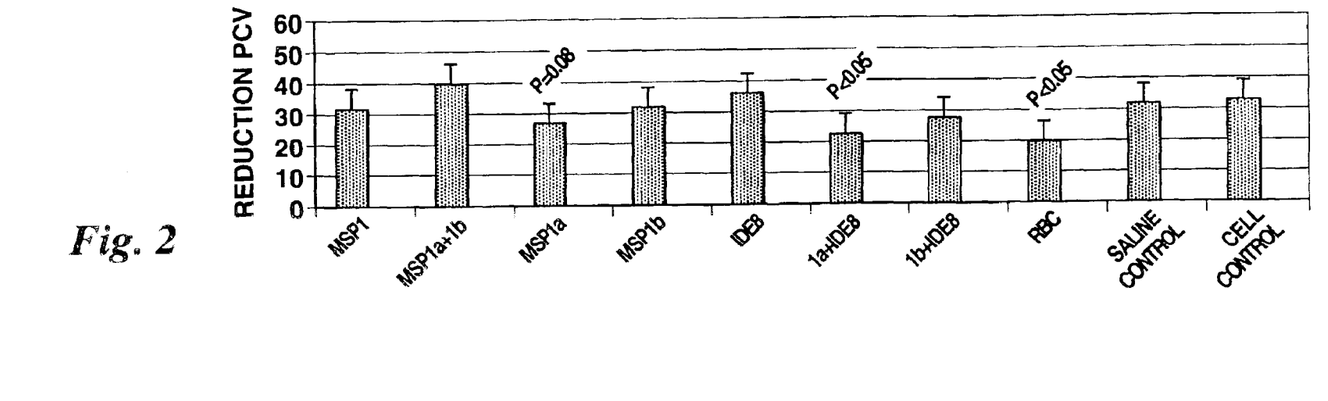
FIG. 2 is a graphical illustration of the reduction in PCV achieved by various combinations of antigens and controls in connection with the experimental results reported herein.

The reduction in PCV, associated with clinical signs, was significantly reduced in cattle immunized with MSP1a combined with infected tick cell-derived antigens and in cattle immunized with erythrocyte-derived antigens (See FIG. 2, wherein Reduction PCV=[(Ave Start PCV-Lowest PCV)/ Start PCV]×100).

The results of these experiments demonstrated that:

a. Cattle immunized with infected tick cell-derived antigens had a preferential recognition for MSP1b while cattle immunized with erythrocyte-derived antigens showed a bias toward MSP1a. The bias in the antibody response against MSP1a or MSP1b in cattle immunized with *A. marginale* antigens from IDE8 tick cells or bovine erythrocytes suggests that the MSP1 complex exposure on the surface of parasites may vary during multiplication on the tick and mammalian hosts;

b. The immunization with the MSP1 complex or with MSP1a and MSP1b together did not protect cattle after challenge with *A. marginale* despite that cattle responded to both antigens; and c. Cattle with a predominant immune response against MSP1a (groups immunized with MSP1a, MSP1a plus infected tick cell-derived antigens and infected erythrocyte-derived antigens) were protected against *A. marginale* infection as demonstrated by the lower reduction in PCV.

It can thus be appreciated that the utilization of recombinant MSP1a in vaccines provides an advantageous mechanism to achieve resistance in cattle against *A. marginale* infection. Whereas erythrocyte-derived *A. marginale* is disadvantaged due to cost, difficulties in purifying antigen from bovine membranes, problems with preventing pathogen contamination and difficulties in standardization, recombinant MSP1a may be readily and cost effectively prepared in a standardized, pure form free of bovine erythrocyte membranes and antigens that might result in formation of an immune response to bovine blood cells.

EXAMPLE 3

Function of MSP1a Tandem Repeats in Adhesion to Host Cell Receptors

1. Construction, expression in *E. coli* and characterization of wild type MSP1a and mutants. A MSP1a (Oklahoma isolate msp1α clone per1 [14]) mutant lacking the tandem repeats was constructed by PCR. Oligonucleotide primers RIOR (5'-CCGAATTCCATGTTAGCGGCTAATTGGCG GCAAGAGATGCG-3') (SEQ. ID NO: 5) and MSP1a3BII (5'-CCAGATCTCTTTACGCCGCCGCC TGCGCC-3') (SEQ. ID NO: 6) were designed to amplify the msp1α gene lacking 6 amino acids preceding the repeats and the tandem repeats in a 50 µl volume PCR (0.2 µM each primer, 1.5 mM MgSO$_4$, 0.2 mM dNTP, 1×AMV/Tfl reaction buffer, 5u Tfl DNA polymerase) employing the Access RT-PCR system (Promega, USA). Reactions were performed in an automated DNA thermal cycler (Eppendorf MASTERCYCLER® personal, USA) for 35 cycles. After an initial denaturation step of 30 sec at 94° C., each cycle consisted of a denaturing step of 30 sec at 94° C. and an annealing-extension step of 2.5 min at 68° C. The program ended by storing the reactions at 4° C. The primers introduced an ATG initiation codon and Eco RI and Bgl II restriction sites for cloning into the pFLAG-CTC expression vector (Sigma). The resulting plasmid pAF0R1 was transformed into *E. coli* JM109 and induced for expression of mutant MSP1a as previously reported for MSP1a [14]. For the expression of MSP1a (Oklahoma isolate msp1α clone per1 [14]) tandem repeats in *E. coli*, this region was amplified using oligonucleotide primers RNOKBS5 (5'-GAGATCTGCT GATGGCTCGTCAGCGGG-3') (SEQ. ID NO: 7) and RNOKBS3 (5'-GGTCGACCCTGATTGAGACGATGT ACTGGCC-3') (SEQ. ID NO: 8). The PCR was conducted as previously described but with amplification cycles consisting of a denaturing step of 30 sec at 94° C., an annealing step of 30 sec at 58° C. and an extension step of 1 min at 68° C. The 5' and 3' amplification primers contained Bgl II and Sal I restriction sites, respectively, for cloning into pFLC1b [14] for expression in *E. coli* as a fusion peptide to the COOH-terminus of MSP1b (locus β1, Oklahoma isolate). The resulting plasmid pF1bRNO4 was transformed into *E. coli* JM109 and induced for expression of mutant MSP1b>MSP1a-repeats protein as previously reported for MSP1b [14]. All constructs were sequenced at the Core Sequencing Facility, Department of Biochemistry and Molecular Biology, Noble Research Center, Oklahoma State University using ABI Prism dye terminator cycle sequencing protocols developed by Applied Biosystems (Perkin-Elmer Corp., Foster City Calif.).

Expression of recombinant mutant proteins was assayed by SDS-PAGE, Western blot or live-cell immunofluorescence assay as previously reported [35]. The hemagglutination of bovine erythrocytes and adhesion to cultured IDE8 tick cells of recombinant *E. coli* expressing the wild type and mutant proteins was evaluated in a microtitre hemagglutination and *E. coli* recovery adhesion assays, respectively, as reported [35].

2. Results. To study the function and structural organization of tandem repeated peptides in MSP1a we selected a recent *A. marginale* field isolate from Oklahoma that is tick-transmissible and for which we have cloned and characterized MSP1a and MSP1b. A recombinant mutant MSP1a was constructed lacking the tandem repeated peptides and expressed in *E. coli*. The recombinant mutant protein was expressed at high levels and was secreted to the *E. coli* membrane as shown by live-cell immunofluorescence. Nevertheless, the adhesion to cultured IDE8 tick cells of recombinant *E. coli* expressing the mutant protein was abolished when compared to the wild type MSP1a (Table 2). To demonstrate that the MSP1a repeats were not only necessary but sufficient to confer adhesion of recombinant *E. coil* to tick cells, we then constructed a chimeric protein containing the MSP1a tandem repeated peptides fused to the COOH-terminus of the MSP1b. MSP1b did not confer an adhesive phenotype when expressed in *E. coli* (Table 3). However, *E. coli* expressing the chimeric protein adhered to cultured IDE8 tick cells at levels comparable to the wild type MSP1a-expressing *E. coli* (Table 3).

The capacity of MSP1a to hemagglutinate bovine erythrocytes was also mediated by the tandem repeats. Recombinant *E. coli* expressing the MSP1a lacking the tandem repeats were unable to hemagglutinate bovine erythrocytes (Table 2) while the chimeric MSP1b>MSP1a-repeats protein expressed in *E. coli* conferred to recombinant bacteria a higher hemagglutination capacity (Table 3) when compared to wild type MSPs.

TABLE 2

Hemagglutination of bovine erythrocytes and adhesion to cultured tick IDE8 cells by recombinant *E. coli* expressing *A. marginale* (Oklahoma isolate) MSP1a wild type and mutant protein without repeats

| | Plasmid carried by recombinant *E. coli* | | | |
|---|---|---|---|---|
| Relevant protein expressed | pFLC1a MSP1a | pAF0R1 MSP1a-no repeats mutant | p33 None | No plasmid None |
| No. of CFU (mean ± SD) recovered from IDE8 cells (N = 3) | 500 ± 141 | 14 ± 18 | 231 ± 129 | 0 |
| Average fold increase over p33 control | 2 | — | — | — |
| P (Student's t-Test) | 0.05 | — | — | — |
| Average fold decrease over MSP1a (OK) | — | 36 | — | — |
| P (Student's t-Test) | — | 0.02 | — | — |
| Hemagglutination of bovine erythrocytes (N = 3)[a] | 1 | 0 | 0 | 0 |

[a]0, no hemagglutination; 1, weak hemagglutination; 2, moderate hemagglutination; 3, near maximum hemagglutination; 4, maximum hemagglutination [7].

TABLE 3

Hemagglutination of bovine erythrocytes and adhesion to cultured IDE8 tick cells of *E. coli* expressing wild type MSP1a or MSP1b (Oklahoma isolate) and MSP1b > MSP1a-repeats mutant proteins

| | Plasmid carried by recombinant *E. coli* | | |
|---|---|---|---|
| Relevant protein expressed | pFLC1a MSP1a | pFLC1b2 MSP1b | PF1bRNO4 MSP1b > MSP1a-repeats |
| No. of CFU recovered from IDE8 cells (Ave ± SD) (N = 2) | 975 ± 742 | 18 ± 17 | 530 ± 325 |
| Average fold increase over pFLC1b2 (MSP1b) | 54 | — | 29 |
| Hemagglutination of bovine erythrocytes (N = 2)[a] | 1 | 4 | 5 |

[a]Plates were incubated for 2 hours at 40° C. and results scored essentially as reported by McGarey and Allred [7]: 0, no hemagglutination; 1, weak hemagglutination; 2, moderate hemagglutination; 3, near maximum hemagglutination; 4, maximum hemagglutination; 5, maximum hemagglutination in 1 hour.

Accordingly, it can be appreciated that subunits derived from MSP1a are useful as well in the inventive vaccine compositions. The inclusion of MSP1a region(s) effecting MSP1a biological function could enhance the host immune response directed against relevant immunoprotective epitopes.

The preparation of vaccines utilizing as distinct antigenic components MSP1a is easily accomplished using well known methods and techniques. The vaccine and/or antigen preparation is combined into a formulation in an amount effective to provide for a protective immune response against infection with *A. marginale*. A protective immune response against *A. marginale* decreases the clinical signs of anaplasmosis. Clinical symptoms of anaplasmosis include a reduction in packed red cell volume of about 25 to 80% and parasitemia of the red blood cells of about 15 to 70%. A decrease in the symptoms of anaplasmosis includes prevention of the reduction in the packed red cell volume and a decrease in percent parasitemia. Preferably, a protective response includes packed red cell volume change of 25% or less compared with control animals and/or a decrease in parasitemia to about 5 to 25% of the red blood cells or less depending on the conditions. Measurements of packed red cell volume and percent parasitemia are conducted using standard methods. Vaccine preparations are combined with physiologically acceptable carriers to form vaccines. The preferred physiologically acceptable carrier is an oil-based adjuvant.

Preferably, the inventive vaccine formulation is set to contain about 100 micrograms of recombinant antigens associated to *E. coli* membranes in an oil-based adjuvant such as XTEND® III (Grand Laboratories, Larchwood, Iowa).

The vaccines may be administered by a variety of routes including intravenously, intraperitoneally, intramuscularly, and subcutaneously. The preferred route of administration is subcutaneous. The vaccine can be administered in a single dose or multiple doses until a protective effect is achieved.

Recombinant Antigen MSP1a from *Anaplasma marginale* to Reduce Infections in Ticks, Vaccine Compositions and Methods of Use It has been discovered that the incorporation of recombinant MSP1a in vaccine formulations against *A. marginale* in combination with infected IDE8 cells-derived antigens and/or pathogen and tick-derived antigens would allow the development of vaccines against anaplasmosis with protection effect on the multiplication of *A. marginale* in the bovine host and an effect on the transmission of the pathogen by the tick vector. *A. marginale* Oklahoma isolate major surface protein 1a (msp1α) gene (AY010247) is provided as SEQ. ID NO: 9, and major surface protein 1a (AAG29248) sequence listing is provided as SEQ. ID NO: 10.

1. Cattle Vaccination and Challenge

Twenty Holstein cattle, 12 to 24 months old, were used for this study. These cattle were selected from 55 cattle used for a larger vaccine trial that were randomly assigned to two experimental groups of 20 cattle each and one group of 15 control cattle in which Group 1 cattle were immunized with three isolates of *A. marginale* derived from tick cell culture (Virginia, Oklahoma and Oregon isolates) and 100 μg recombinant MSP1a; Group 2 cattle were immunized with 100 μg of recombinant MSP1a; and cattle in Group 3 were left unvaccinated to serve as controls for natural infection conditions.

It has been demonstrated that *A. marginale* infection levels in ticks fed on cattle immunized with *E. coli* membranes and uninfected cultured IDE8 tick cell-derived antigens were similar to the infection levels in ticks fed on non-immunized cattle.

Ten immunized cattle were selected for this study based on detection of high antibody titers against recombinant MSP1a. Of these ten cattle, 5 were chosen from Group 1 (cattle 226, GT168, 242, 294, 141) and 5 were chosen from Group 3. Cattle GT165, GT155, 219, 248, GT152) for the non-immunized controls, ten cattle (214, 210, 245, 251, 143, 157, 247, 217, 166, 162) were randomly chosen out of the 15 control cattle from the larger study.

*A. marginale* antigens from infected IDE8 cells were prepared as described previously [20,22]. Recombinant MSP1a was prepared by inducing the expression of the protein in *E. coli* [18]. The *E. coli* cells were then disrupted by sonication followed by centrifugation for separation of soluble from membrane bound antigens. The resulting pellet that contained the MSP1a in *E. coli* membranes was used for immunization. The total protein concentration was determined and the amount of recombinant MSP1a was estimated from Western blots using affinity purified recombinant MSP1a as standard [22].

Cattle were immunized at weeks 4 and 8 with a 5 ml dose containing the antigen in an oil-based adjuvant (Adjuvant XTEND® III Grand Laboratories, Larchwood, Iowa, USA) [20]. Cattle were challenge-exposed two weeks after the last immunization by intravenous administration of 1.7 ml infected blood containing $10^9$ *A. marginale*. The challenge-exposure blood was obtained from a splenectomized calf that was experimentally infected with the Virginia isolate of *A. marginale* (calf PA481, percent infected erythrocytes (PPE) of 10.4%, packed cell volume (PCV) of 31.5%). Parameters used for evaluation of cattle included determination of the PPE and PCV. Whole blood was collected in vacutainer tubes containing EDTA and used for preparation of stained blood smears for light microscopy and for determination of the PCV. Serum samples were collected from each animal upon purchase, at weeks 4 and 8 just prior to immunization, at week 10 and during tick feeding. Serum samples were stored at −70° C. until tested by ELISA and Western blots for determination of MSP1a antibody titers.

2. Identification of Cattle with High Antibody Liters to MSP1a, Tick Feeding Studies and Determination of *A. marginale* Infection Levels in Tick Salivary Glands.

Serum samples collected from cattle two weeks after the last immunization were analyzed as described previously by ELISA and Western blots for recognition of recombinant MSP1a [22]. Ten immunized animals with the highest titers against MSP1a by Western blot were selected from groups 1 and 2 (5 animals from each). Ten control animals from group 3 were randomly selected and sera from these cattle were proven to be negative for MSP1a antibodies by Western blot.

Each of the 20 cattle were infested with 60 male *D. variabilis* that were reared at the Oklahoma State University, Centralized Tick Rearing Facility. The ticks were placed in an orthopedic stockinettes glued to the cow's side when *A. marginale* infection was observed in stained blood smears. The ticks were allowed to feed on cattle for seven days, after which they were removed and held in humidity for 5 days. The ticks were then allowed to feed for 7 days on a sheep to stimulate development of *A. marginale* into tick salivary glands. The ticks were then removed from the sheep and the salivary glands from 20 ticks (40 salivary glands) were dissected and pooled in 500 µl RNALater (Ambion). DNA was extracted from groups of 40 salivary glands and then used in a quantitative msp4 PCR to quantify *A. marginale* infection levels [19, 22].

3. Statistical Analysis

For the analysis of the PPE and percent reduction PCV values between immunized and control cattle, pair wise comparisons (Student's t-test) were conducted. Salivary gland infection levels between ticks fed on vaccinated and control cattle were compared by Student's t-test. A correlation analysis between tick salivary gland infection levels and antibody titers against MSP1a in cattle during tick feeding was performed using Microsoft Excel 2000.

4. Results

Cattle chosen for these studies after vaccination and prior to challenge-exposure and tick feeding were based on high antibody titers to MSP1a Serum samples collected two weeks after the last immunization were analyzed by Western blot for recognition of MSP1a and 10 immunized animals with the highest titers against MSP1a were identified. Ten control animals were confirmed negative for MSP1a antibodies by Western blot. Mean peak PPE (3.6±2.6 and 3.2±1.7 for control and immunized cattle, respectively) and mean percent reduction of PCVs (29.3±7 and 26.8±12.2 for control and immunized cattle, respectively) of immunized and control cattle during tick feeding were not significantly (P>0.05) (Table 4).

TABLE 4

Peak percent parasitized erythrocytes during tick feeding on cattle, anti-MSP1a antibody titers, infection in tick salivary glands and inhibition of infection of *A. marginale* in ticks that acquired infection on immunized and control cattle.

| Experimental groups | Cattle number[a] | Immunogen | Peak PPE during tick feeding[b] | Anti-MSP1a antibody titers[c] | Tick infection levels (copies msp4/ salivary gland)[d] | Inhibition of tick infection[e] |
|---|---|---|---|---|---|---|
| Vaccinated | GT 152 | Recombinant MSP1a | 0.3 | 1600 | 0.1 | 100% |
| | GT 155 | | 1.6 | <100 | 14 | 93.5% |
| | GT 165 | | 5.8 | 1600 | 80 | 62.6% |
| | 219 | | 4.5 | 200 | 2 | 99.1% |
| | 248 | | 3.2 | 800 | 14 | 93.5% |
| | 141 | IDE8-derived *A. marginale* plus recombinant MSP1a | 4.1 | <100 | 25 | 88.3% |
| | GT 168 | | 1.6 | <100 | 2 | 99.1% |
| | 226 | | 5.0 | 400 | 2 | 99.1% |
| | 242 | | 3.0 | 400 | 14 | 93.5% |
| | 294 | | 2.8 | 200 | 25 | 88.3% |
| Control | 143 | None | 4.3 | <100 | 140 | — |
| | 157 | | 0.5 | 100 | 0.4 | — |
| | 162 | | 3.5 | 100 | 25 | — |
| | 166 | | 2.5 | <100 | 795 | — |
| | 210 | | 3.2 | 100 | 2 | — |
| | 214 | | 1.9 | 100 | 80 | — |
| | 217 | | 1.6 | 100 | 140 | — |
| | 245 | | 2.4 | 100 | 25 | — |
| | 247 | | 6.9 | 400 | 140 | — |
| | 251 | | 9.2 | 100 | 795 | — |

[a]Cattle were analyzed for antibody response against recombinant MSP1a before challenge-exposure. Ten immunized animals showing the highest titers against MSP1a and 10 controls with sera negative for MSP1a in the Western blot were selected.
[b]The percent infected erythrocytes (PPE) was determined in blood smears of samples collected daily during the 7 days of tick acquisition-feeding.
[c]Values correspond to the maximum dilution that gave an $OD_{450\,nm}$ equal or higher than mean background + 2 SD.
[d]DNA was extracted from 40 salivary glands and used in a quantitative PCR to determine *A. marginale* infection levels. The number of msp4 copies was calculated as $10^{[(\log Ta - 0.5)/0.4]}$.
[e]The inhibition of tick infection was determined as [1 − (Infection level/Mean control infection level)] × 100.

Antibody titers against MSP1a were determined by ELISA in sera obtained after tick infestation and compared between immunized and control cattle (Table 1). The average anti-MSP1a antibody titers in immunized cattle (520±153; mean±SE) was higher (P=0.03) than in control cattle (110±34).

*A. marginale* infection levels in salivary glands from ticks that fed on rickettsemic immunized and control cattle are listed in Table 1. Although infection levels varied among individual ticks, the number of msp4 copies per salivary gland was higher (P=0.04) in ticks fed on control cattle (214±98; mean±SE) when compared to ticks that fed on immunized cattle (18±8). Differences were not observed between ticks fed on cattle immunized with recombinant MSP1a or with IDE8-derived *A. marginale* together with recombinant MSP1a. The average inhibition of tick infection in ticks that fed on the immunized cattle was 91.7% (range 62.69%–100.0%) (Table 4).

Differences in infection rates between ticks that fed on immunized and control cattle did not appear to be affected by the *A. marginale* infections in cattle or the percent reduction PCVs during tick feeding. The PPEs in the cattle were not statistically different among groups and the percent reduction PCVs were not low enough to affect tick feeding.

The results reported herein demonstrated that anti-MSP1a antibodies in vaccinated cattle reduced infection of *A. marginale* for *D. variabilis*. Differences in salivary gland infection levels between ticks fed on immunized and control cattle agreed with statistically significant differences in the anti-MSP1a antibody titers between immunized and control cattle after tick infestation. Difference in the results obtained after vaccination with recombinant MSP1a compared to the antibody response generated after *A. marginale* infection of cattle could be explained by differences in the anti-MSP1a antibody levels and/or by differences in the MSP1a epitopes recognized by the antibodies. The recombinant MSP1a protein is presented separately to the bovine immune system, rather than as a complex with MSP1b, which appears to allow for recognition of all the epitopes in the region containing the tandem repeats involved in adhesion of MSP1a to tick cells [15]. The antibodies against the native MSP1a may not be directed against the neutralizing domain masked by the structure of the MSP1 complex.

Comparison of the data obtained from cattle vaccinated with recombinant MSP1a or with IDE8-derived *A. marginale* together with recombinant MSP1a suggested that the antibody response against IDE8 and IDE8-derived *A. marginale* antigens, other than MSP1a, had little or no inhibitory effect on tick infection. The antibody response against MSP1a inhibited but did not prevent infection of ticks by *A. marginale*. As was reported in previous studies [18, 36], salivary gland infection levels were variable and reflected variation among individual ticks. Although the effect on the transmission of *A. marginale* by ticks fed on vaccinated cattle is unknown, this study suggests that MSP1a may be necessary but not sufficient for infection of ticks by *A. marginale*. Alternatively, over expression of MSP1a in erythrocytic stages of *A. marginale* and/or the native structure of MSP1a may prevent the complete neutralization of the ligand.

A desirable goal for a vaccine for the control of anaplasmosis is to have a protection effect on the multiplication of *A. marginale* in a bovine host and a blocking effect on the transmission of the pathogen by the tick vector. The results reported herein support the role of MSP1a in the transmission of *A. marginale* by ticks and suggest the incorporation of recombinant MSP1a in vaccine formulations against *A. marginale* in combination with infected IDF8 cells-derived antigens and/or as yet unidentified pathogen and tick-derived antigens.

While the invention has been been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

Bibliography

Each of the following publicly available documents is incorporated herein by reference.

[1] Ristic, M. and A. M. Watrach. 1963. Anaplasnosis. VI. Studies and a hypothesis concerning the cycle of development of the causative agent. Am. J. Vet. Res. 24:67–276.

[2] Kuttler, K. L. 1984. *Anaplasma* infections in wild and domestic ruminants: a review. J. Wild. Dis. 20:12–20.

[3] Dikinans, G. 1950. The transmission of anaplasmosis. Am. J. Vet. Res. 11:5–16.

[4] Ewing, S. A. 1981. Transmission of *Anaplasma marginale* by arthropods. In: Proc. $7^{th}$ Nat Anaplasmosis Conf. Mississippi State University, MS, USA, pp. 395–423.

[5] Kocan, K. M. 1986. Development of *Anaplasma marginale*: coordinated development of a rickettsial organisms and its tick host. In: Sauer J R, Hair J A, editors. Morphology, Physiology and Behavioral Ecology of Ticks. Chichester: Horwood, pp.472–505.

[6] Kocan, K. M., D. Stiller, W. L. Goff, P. L. Claypool, W. Edwards, S. A. Ewing, T. C. McGuire, J. A. Hair, and S. J. Barron. 1992. Development of *Anaplasma marginale* in male *Dermacentor andersoni* transferred from infected to susceptible cattle. Am. J. Vet. Res. 53:499–507.

[7] Ge, N. L., K. M. Kocan, E. F. Blouin, and G. L. Murphy. 1996. Developmental studies of *Anaplasma marginale* (Rickettsiales: Anaplasmataceae) in male *Dermacentor andersoni* (Acari:Ixodidae) infected as adults using non-radioactive in situ hybridization. J. Med. Ent. 33: 911–920.

[8] Kocan, K. M., W. L. Goff, D. Stiller, P. L. Claypool, W. Edwards, S. A. Ewing, J. A. Hair, and S. J. Barron. 1992. Persistence of *Anaplasma marginale* (Rickettsiales: Anaplasmataceae) in male *Dermacentor andersoni* (Acari: Ixodidae) transferred successively from infected to susceptible cattle. J. Med. Ent. 29:657–668.

[9] Melendez R D, K. M. Kocan, A. A. Guglielmone and J. de la Fuente. 2002. *Anaplasma marginale*: Antigens and control alternatives for a rickettsial hemoparasite of cattle. Clin. Micro. Rev. Submitted June.

[10] Palmer, G. H. 1989. Anaplasmosis vaccines, In: I G Wright, ed. *Veterinary Protozoan and Hemoparasite Vaccines*. Boca Raton (Fla.): CRC Press, pp. 1–29.

[11] Allred, D. R., T. C. McGuire, G. H. Palmer, S. R. Leib, T. M. Harkins, T. F. McElwain and A. F. Barbet. 1990. Molecular basis for surface antigen size polymorphisms and conservation of a neutralization-sensitive epitope in *Anaplasma marginale*. Proc. Nat. Acad. Sci. U.S.A. 87:3220–3224.

[12] Palmer, G. H., F. R. Rurangirwa, T. F. and T. F. McElwain. 2001. Strain composition of the ehrlichia *Anaplasma marginale* within persistently infected cattle, a mammalian reservoir for tick transmission J. Clin. Microbiol. 39:631–635.

[13] Bowie, M. V., J. de la Fuente, K. M. Kocan, E. F. Blouin, and A. F. Barbet. 2001. Conservation of major surface protein 1 genes of the ehrlichial pathogen *Anaplasma marginale* during cyclic transmission between ticks and cattle. Gene 282:95–102.

[14] de la Fuente, J., J. C. Garcia-Garcia, E. F. Blouin, S. D. Rodriguez, M. A. Garcia, and K. M. Kocan. 2001a. Evolution and function of tandem repeats in the major surface protein 1a of the ehrlichial pathogen *Anaplasma marginale*. An. Health Res. Rev. 2:163–173.

[15] de la Fuente, J., J. C. Garcia-Garcia, E. F. Blouin, and K. M. Kocan. 2002a. Characterization of the functional domain of major surface protein 1a involved in adhesion of the rickettsia *Anaplasma marginale* to host cells. Vet. Microbiol. In press.

[16] McGarey, D. J., A. F. Barbet, G. H. Palmer, T. C. McGuire and D. R. Allred. 1994. Putative adhesins of *Anaplasma marginale*: major surface polypeptides 1a and 1b. Infect. Immun. 62:4594–4601.

[17] McGarey, D. J. amd D. R. Allred. 1994. Characterization of hemagglutinating components on the *Anaplasma*

*marginale* initial body surface and identification of possible adhesins. Infect. Immun. 62:4587–4593.

[18] de la Fuente, J., J. C. Garcia-Garcia, E. F. Blouin, and K. M. Kocan. 2001b. Differential adhesion of major surface proteins 1a and 1b of the ehrlichial cattle pathogen *Anaplasma marginale* to bovine erythrocytes and tick cells. Int. J. Parasitol. 31:145–153.

[19] de la Fuente, J., J. C. Garcia-Garcia, E. F. Blouin and K. M. Kocan. (2001c). Major surface protein 1a effects tick infection and transmission of the ehrlichial pathogen *Anaplasma marginale*. Int. J. Parasitol. 31:1705–1714.

[20] Kocan, K. M., T. Halbur, E. F. Blouin, V. Onet, J. de la Fuente, J. C. Garcia-Garcia and J. T. Saliki. 2001. Immunization of cattle with *Anaplasma marginale* derived from tick cell culture. Vet. Parasitol. 102:151–161.

[21] Brown, W. C., T. C. McGuire, D. Zhu, H. A. Lewin, J. Sosnow, and G. H. Palmer. 2001. Highly conserved regions of the immunodominant major surface protein 2 of the genogroup II ehrlichial pathogen *Anaplasma marginale* are rich in naturally derived CD4(+) T lymphocyte epitopes that elicit strong recall responses. J. Immunol. 166:1114–1124.

[22] de la Fuente, J., K. M. Kocan, J. C. Garcia-Garcia, E. F. Blouin, P. L. Claypool, P. L., J. T. Saliki. 2002b. Vaccination of cattle with *Anaplasma marginale* derived from tick cell culture and bovine erythrocytes followed by challenge-exposure by infected ticks. Vet. Microbiol. 89: 239–251.

[23] Blouin, E. F., J. de la Fuente, J., J. C. Garcia-Garcia, J. R. Sauer, J. T. Saliki, and K. M. Kocan. 2002a. Use of a cell culture system for studying the interaction of *Anaplasma marginale* with tick cells. Animal Health Res. Rev. In press.

[24] Blouin, E. F., J. T. Saliki, J. de la Fuente, J. C. Garcia-Garcia, J. C. and K. M. Kocan. 2002b. Antibodies to *Anaplasma marginale* Major Surface Protein 1a and 1b inhibit infectivity for cultured tick cells. Vet. Parasitol. (Submitted).

[25] Brock, W. E., I. O. Kliewer and C. C. Pearson. 1965. A vaccine for anaplasmosis. J. Am. Vet. Med. Assoc.147:943–951.

[26] Palmer, G. H., S. D. Waghela, A. F. Barbet, W. C. Davis and T. C. McGuire. 1987. Characterization of a neutralization sensitive epitope on the AM 105 surface protein of *Anaplasma marginale*. J. Parasitol. 17:1279–1285.

[27] Hart, L. T., W. J. Todd and D. G Luther. 1990. *Anaplasma marginale* antigen, antigen composition, vaccine and process for production of said antigen, antigen composition and vaccine. U.S. Pat. No. 4,956,278.

[28] Montenegro-James, S., M. A. James, M. Toro Benitez, E. Leon, B. K. Baek and A. T. Guillen. 1991. Efficacy of purified *Anaplasma marginale* initial bodies as a vaccine against anaplasmosis. Parasitol. Res. 77:93–101.

[29] McGarey D J, Barbet A F, Palmer G H, McGuire T C, Allred D R. Putative adhesins of *Anaplasma marginale*: major surface polypeptides 1a and 1b. Infect Immun 1994; 62: 4594–4601.

[30] Oberle S M, Palmer G H, Barbet A F, McGuire T C. Molecular size variations in an immunoprotective protein complex among isolates of *Anaplasma marginale*. Infect Immun 1988; 56:1567–1573.

[31] Allred D R, McGuire T C, Palmer G H, Leib S R, Harkins T M, McElwain T F, Barbet A F. Molecular basis for surface antigen size polymorphisms and conservation of a neutralization-sensitive epitope in *Anaplasma marginale*. Proc Natl Acad Sci USA 1990; 87: 3220–3224.

[32] de la Fuente, J., van den Bussche, R. A., Kocan, K. M. Molecular phylogeny and biogeography of North American isolates of *Anaplasma marginale*. Veterinary Parasitology 2001; 97: 65–76.

[33] Palmer G H, Waghela S D, Barbet A F, Davis W C, McGuire T C. Characterization of a neutralization-sensitive epitope on the AM 105 surface protein of *Anaplasma marginale*. J Parasitol 1987; 17: 1279–1285.

[34] Viseshakul N, Kamper S, Bowie M V, Barbet A F. Sequence and expression analysis of a surface antigen gene family of the rickettsia *Anaplasma marginale*. Gene 2000; 253: 45–53.

[35] de la Fuente, J., Garcia-Garcia, J. C., Blouin, E. F., Kocan, K. M. Differential adhesion of major surface proteins 1a and 1b of the ehrlichial cattle pathogen *Anaplasma marginale* to bovine erythrocytes and tick cells. Int. J. Parasitol. 2001; 31: 145–153.

[36] Kocan K. M. and J. de la Fuente. 2002. Co-feeding studies of ticks infected with *Anaplasma marginale*. Vet. Parasitol. Submitted July.

[37] Palmer G H, Barbet A F, Cantor G H, McGuire T C. Immunization of cattle with the MSP-1 surface protein complex induces protection against a structurally variant *Anaplasma marginale* isolate. Infect Immun 1989; 57: 3666–3669.

[ ] Kocan K M, Blouin E F, Barbet A F. Anaplasmosis control: past, present and future. Ann NY Acad Sci, 2000; 916: 501–509.

[ ] Barbet A F, Palmer G H, Myler P J, McGuire T C. Characterization of an immunoprotective protein complex of *Anaplasma marginale* by cloning and expression of the gene coding for polypeptide AM 105L. Infect Immun1987; 55: 2428–2435.

[ ] McGarey D J, Allred D R. Characterization of hemagglutinating components on the *Anaplasma marginale* initial body surface and identification of possible adhesins. Infect Immun 1994; 62: 4587–4593.

[ ] Munderloh U G, Blouin E F, Kocan K M, Ge N L. Establishment of the tick (Acari: Ixodidae)-borne cattle pathogen *Anaplasma marginale* (Rickettsiales: Anaplasmataceae) in tick cell culture. J Med Ent 1996; 33: 656–664.

[ ] Blouin E F, Barbet A F, Jooyoung Yi, Kocan K M, Saliki J T. Establishment and characterization of an Oklahoma isolate of *Anaplasma marginale* in cultured *Ixodes scapularis* cells. Vet Parasitol 1999; 87: 301–313.

[ ] Blouin E F, Kocan K M. Morphology and development of *Anaplasma marginale* (Rickettsiales: Anaplasmataceae) in cultured *Ixodes scapularis* (Acari: Ixodidae) cells. J Med Entomol 1998; 35: 788–797.

[ ] Barbet A F, Blentlinger R, Jooyoung Yi, Lundgren A M, Blouin E F, Kocan K M. Comparison of surface proteins of *Anaplasma marginale* grown in tick cell culture, tick salivary glands, and cattle. Infect Immun1999; 67: 102–107.

[ ] Barbet, A. F., R. Blentlinger, J. Yi, A. M. Lundgren, E. F. Blouin, and K. M. Kocan. 1999. Comparison of surface proteins of *Anaplasma marginale* grown in tick cell culture, tick salivary glands, and cattle. Infect. Immun. 67:102–107.

[ ] Eid, G., D. M. French, A. M. Lundgren, A. F. Barbet, T. F. McElwain, and G. H. Palmer. 1996. Expression of major surface protein 2 antigenic variants during acute *Anaplasma marginale* rickettsemia. Infect. Immun. 64:836–841.

[ ] Kocan K. M., E. F. Blouin G. H. Palmer, I. S. Eriks and W. L. Edwards. 1996. Preliminary studies on the effect of *Anaplasma marginale* antibodies ingested by *Dermacentor andersoni* ticks (Acari: Ixodidae) with their bloodmeal on infections in salivary glands. Exp. Appl. Acarol. 20:297–311.

What is claimed is:

1. A method for reducing *A. marginale* infection in ticks, said method comprising: administering to a ruminant population susceptible to tick infection a composition comprising recombinant MSP1a and an immunogen derived from *A. marginale*; wherein said immunogen is not MSP1b and said composition further comprises a pharmaceutically acceptable carrier or diluent; and allowing said ticks to feed on said ruminants.

2. The method according to claim 1, wherein approximately 100 μg of said recombinant MSP1a is administered.

3. The method according to claim 1, wherein said immunogen is tick cell culture derived *A. marginale*.

4. The method according to claim 3, wherein said tick cell culture comprises *Ixodes scapularis* tick cell line IDE8.

5. The method according to claim 1, wherein said recombinant MSP1a is from the Oklahoma isolate of *A. marginale*.

6. The method according to claim 3, wherein said tick cell culture derived *A. marginale*, is selected from the group consisting of the Oklahoma, Virginia and Oregon isolates of *A. marginale*.

7. The method according to claim 3, wherein said composition contains approximately $2 \times 10^{10}$ *A. marginale*.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: artificial
<220> FEATURE:
<223> OTHER INFORMATION: oligonucleotide primer

<400> SEQUENCE: 1
gcattacaac gcaacgcttg ag                                        22

<210> SEQ ID NO 2
<211> LENGTH: 22
<212> TYPE: DNA
<213> ORGANISM: artificial
<220> FEATURE:
<223> OTHER INFORMATION: oligonucleotide primer

<400> SEQUENCE: 2
gctttacgcc gccgcctgcg cc                                        22

<210> SEQ ID NO 3
<211> LENGTH: 30
<212> TYPE: DNA
<213> ORGANISM: artificial
<220> FEATURE:
<223> OTHER INFORMATION: oligonucleotide primer

<400> SEQUENCE: 3
ccgctcgaga tgttagcgga gtatgtgtcc                                30

<210> SEQ ID NO 4
<211> LENGTH: 24
<212> TYPE: DNA
<213> ORGANISM: artificial
<220> FEATURE:
<223> OTHER INFORMATION: oligonucleotide primer

<400> SEQUENCE: 4
gaagatctcg ccgccgcctg cgcc                                      24

<210> SEQ ID NO 5
<211> LENGTH: 41
<212> TYPE: DNA
<213> ORGANISM: artificial
<220> FEATURE:
<223> OTHER INFORMATION: oligonucleotide primer

<400> SEQUENCE: 5
ccgaattcca tgttagcggc taattggcgg caagagatgc g                   41

<210> SEQ ID NO 6
<211> LENGTH: 29
<212> TYPE: DNA
<213> ORGANISM: artificial
<220> FEATURE:
<223> OTHER INFORMATION: oligonucleotide primer

<400> SEQUENCE: 6
ccagatctct ttacgccgcc gcctgcgcc                                 29

<210> SEQ ID NO 7
<211> LENGTH: 27

```
<212> TYPE: DNA
<213> ORGANISM: artificial
<220> FEATURE:
<223> OTHER INFORMATION: oligonucleotide primer

<400> SEQUENCE: 7
gagatctgct gatggctcgt cagcggg                                           27

<210> SEQ ID NO 8
<211> LENGTH: 31
<212> TYPE: DNA
<213> ORGANISM: artificial
<220> FEATURE:
<223> OTHER INFORMATION: oligonucleotide primer

<400> SEQUENCE: 8
ggtcgacccc t gattgagacg atgtactggc c                                    31

<210> SEQ ID NO 9
<211> LENGTH: 2154
<212> TYPE: DNA
<213> ORGANISM: Anaplasma marginale

<400> SEQUENCE: 9
gcattacaac gcaacgcttg agtgatgttt acggctgtag tattgtgctt atggcagaca       60
tttccatata ctgtgcagta cggttgtgct ccccaattgt taaaatttag tatattaatc      120
ttgcgattac acgttccgta tgttacaatc aggccgccgg tgtggtagcg tgctggttgt      180
gtggttgtcc tctttcccga tgttgggtcg ttcgttttac gtcgcacaag tttgtacgct      240
gtgcccctgg cagtgtaggg tttatttgtt tgtgtgtgtg ttatgttagc ggagtatgtg      300
tccccccagc cagctgatgg ctcgtcagcg ggtggtcagc agcaagagag tagtgtgtca      360
tctcaaagtg atcaggccag tacatcgtct caattaggag ctgatagctc gtcagcgggt      420
ggtcagcagc aagagagtag tgtgtcatct caaagtggtc aggccagtac atcgtctcaa      480
ttagggactg atagctcgtc agcgagtggt cagcagcaag agagtagtgt gtcatctcaa      540
agtggtcagc cagtacatc gtctcaatca ggagctaatt gcggcaaga gatgcgctcc        600
aaggttgcga gtgttgagta cattttggct gctcgtgccc ttatttctgt aggggtctat      660
gctgctcagg gagagatcgc gaaatcgcaa ggtgtgctc ccctgcgtgt tgcagaagtc       720
gaagaaatcg tgagggatgg ccttgtacgc agccactttc atgatagtgg cctttcacta      780
ggctccatac gactcgtgct tatgcaggtt ggggataagt tggggctaca aggttttgaag     840
attggcgaag ggtacgccac ctatctcgcg caagcgtttg ctgacaacgt ggtggttgcg      900
gctgatgttc aaagtggtgg tgcgtgctct gccagccttg acagcgcgat cgcaaacgtt      960
gagacgtcgt ggtccctgca cggcggcctg gtaagcaaag attttgaccg tgataccaaa     1020
gtagaaaggg gcgaccttga ggcttttgtc gacttcatgt ttggcggtgt gtcgtacaat     1080
gatgggaacg cgtctgcggc taggagcgta ttggaaacgc ttgccgggca cgtcgatgca     1140
cttggtatat cgtacaatca gctggataag cttgatgctg acactttgta tagtgtcgta     1200
tcgtttagtg ccggttccgc aatagacaga ggtgcggtta gcgatgcggc tgacaagttc     1260
cgtgtgatga tgtttggtgg tgctcctgcg gggcaagaga aaactgccga acctgagcat     1320
gaggctgcga ccccgtcagc tagtagcgtt ccgtcaactg tgcatggtaa ggtcgttgat     1380
gcagttgacc gtgcaaaaga agcggctaag caggcctatg caggcgtgcg taagcggtat     1440
gtggcgaagc cttcggacac tactacacag cttgttgtag ctatcacggc gctgcttatc     1500
```

-continued

```
acggcgtttg ctatctgtgc gtgtttggaa cctaggctta tagggcgtc cggtccgctg      1560 atttggggct gcctggcact agtagcactg ctgccattac ttggtatggc tgtgcatacg      1620
gcagtgagtg cttcgagtca aaagaaggct gccggtggtg cgcaacgggt tgctgctcag      1680
gagaggtcta gggaattgtc ccgtgcgaga caggaagatc agcagaagtt gcatgttccc      1740
gcgatactga ccgggttgag cgtgcttgtg tttattgctg ccgtcgtggc ttgtattgct      1800
gttgacgcga ggcgcgggac gtggcaggc agcatatgtt tcctagccgc atttgtgttg      1860
tttgcgatca gtgccgctgt tgtaatggca acacgtgacc aatcgttggc agaagagtgt      1920
gatagcaagt gtgctacagc tcgtacggct caagctgtac ccggtggcca gcagcagccg      1980
cgtgctaccg agggcgttgt tagcggtggc agccaagaag gcggggctgg tgttcccgga      2040
acttccgtgc cgtcagccgg gtctgggtcc gtacctcctg ctaccattat ggtcagtgtg      2100
gatccacaac ttgttgctac tttgggagca ggtgtggcgc aggcggcggc gtaa             2154
```

<210> SEQ ID NO 10
<211> LENGTH: 623
<212> TYPE: PRT
<213> ORGANISM: Anaplasma marginale

<400> SEQUENCE: 10

```
Met Leu Ala Glu Tyr Val Ser Pro Gln Pro Ala Asp Gly Ser Ser Ala
1               5                   10                  15

Gly Gly Gln Gln Gln Glu Ser Ser Val Ser Ser Gln Ser Asp Gln Ala
            20                  25                  30

Ser Thr Ser Ser Gln Leu Gly Ala Asp Ser Ser Ala Ser Gly Gly Gln
        35                  40                  45

Gln Gln Glu Ser Ser Val Ser Ser Gln Ser Gly Gln Ala Ser Thr Ser
    50                  55                  60

Ser Gln Leu Gly Thr Asp Ser Ser Ala Ser Gly Gln Gln Gln Glu
65                  70                  75                  80

Ser Ser Val Ser Ser Gln Ser Gly Gln Ala Ser Thr Ser Ser Gln Ser
                85                  90                  95

Gly Ala Asn Trp Arg Gln Glu Met Arg Ser Lys Val Ala Ser Val Glu
            100                 105                 110

Tyr Ile Leu Ala Ala Arg Ala Leu Ile Ser Val Gly Val Tyr Ala Ala
        115                 120                 125

Gln Gly Glu Ile Ala Lys Ser Gln Gly Cys Ala Pro Leu Arg Val Ala
    130                 135                 140

Glu Val Glu Glu Ile Val Arg Asp Gly Leu Val Arg Ser His Phe His
145                 150                 155                 160

Asp Ser Gly Leu Ser Leu Gly Ser Ile Arg Leu Val Leu Met Gln Val
                165                 170                 175

Gly Asp Lys Leu Gly Leu Gln Gly Leu Lys Ile Gly Glu Gly Tyr Ala
            180                 185                 190

Thr Tyr Leu Ala Gln Ala Phe Ala Asp Asn Val Val Ala Ala Asp
        195                 200                 205

Val Gln Ser Gly Gly Ala Cys Ser Ala Ser Leu Asp Ser Ala Ile Ala
    210                 215                 220

Asn Val Glu Thr Ser Trp Ser Leu His Gly Gly Leu Val Ser Lys Asp
225                 230                 235                 240

Phe Asp Arg Asp Thr Lys Val Glu Arg Gly Asp Leu Glu Ala Phe Val
                245                 250                 255

Asp Phe Met Phe Gly Gly Val Ser Tyr Asn Asp Gly Asn Ala Ser Ala
```

-continued

```
            260                 265                 270
Ala Arg Ser Val Leu Glu Thr Leu Ala Gly His Val Asp Ala Leu Gly
            275                 280                 285

Ile Ser Tyr Asn Gln Leu Asp Lys Leu Asp Ala Asp Thr Leu Tyr Ser
            290                 295                 300

Val Val Ser Phe Ser Ala Gly Ser Ala Ile Asp Arg Gly Ala Val Ser
305                 310                 315                 320

Asp Ala Ala Asp Lys Phe Arg Val Met Met Phe Gly Gly Ala Pro Ala
                325                 330                 335

Gly Gln Glu Lys Thr Ala Glu Pro Glu His Glu Ala Ala Thr Pro Ser
                340                 345                 350

Ala Ser Ser Val Pro Ser Thr Val His Gly Lys Val Val Asp Ala Val
                355                 360                 365

Asp Arg Ala Lys Glu Ala Ala Lys Gln Ala Tyr Ala Gly Val Arg Lys
                370                 375                 380

Arg Tyr Val Ala Lys Pro Ser Asp Thr Thr Gln Leu Val Val Ala
385                 390                 395                 400

Ile Thr Ala Leu Leu Ile Thr Ala Phe Ala Ile Cys Ala Cys Leu Glu
                405                 410                 415

Pro Arg Leu Ile Gly Ala Ser Gly Pro Leu Ile Trp Gly Cys Leu Ala
                420                 425                 430

Leu Val Ala Leu Leu Pro Leu Leu Gly Met Ala Val His Thr Ala Val
                435                 440                 445

Ser Ala Ser Ser Gln Lys Lys Ala Ala Gly Gly Ala Gln Arg Val Ala
                450                 455                 460

Ala Gln Glu Arg Ser Arg Glu Leu Ser Arg Ala Arg Gln Glu Asp Gln
465                 470                 475                 480

Gln Lys Leu His Val Pro Ala Ile Leu Thr Gly Leu Ser Val Leu Val
                485                 490                 495

Phe Ile Ala Ala Val Val Ala Cys Ile Ala Val Asp Ala Arg Arg Gly
                500                 505                 510

Thr Trp Gln Gly Ser Ile Cys Phe Leu Ala Ala Phe Val Leu Phe Ala
                515                 520                 525

Ile Ser Ala Ala Val Val Met Ala Thr Arg Asp Gln Ser Leu Ala Glu
                530                 535                 540

Glu Cys Asp Ser Lys Cys Ala Thr Ala Arg Thr Ala Gln Ala Val Pro
545                 550                 555                 560

Gly Gly Gln Gln Gln Pro Arg Ala Thr Glu Val Val Ser Gly Gly
                565                 570                 575

Ser Gln Glu Gly Gly Ala Gly Val Pro Gly Thr Ser Val Pro Ser Ala
                580                 585                 590

Gly Ser Gly Ser Val Pro Pro Ala Thr Ile Met Val Ser Val Asp Pro
                595                 600                 605

Gln Leu Val Ala Thr Leu Gly Ala Gly Val Ala Gln Ala Ala Ala
                610                 615                 620
```